US00PP19987P3

(12) United States Plant Patent
Drewlow

(10) Patent No.: US PP19,987 P3
(45) Date of Patent: May 12, 2009

(54) ***KALANCHOE* PLANT NAMED 'FOREVER MIDI CORAL'**

(50) Latin Name: *Kalanchoe blossfeldiana*
Varietal Denomination: Forever Midi Coral

(75) Inventor: Lyndon W. Drewlow, Lompoc, CA (US)

(73) Assignee: The Paul Ecke Ranch, Encinitas, CA (US)

( * ) Notice: Subject to any disclaimer, the term of this patent is extended or adjusted under 35 U.S.C. 154(b) by 221 days.

(21) Appl. No.: 11/728,029

(22) Filed: Mar. 23, 2007

(65) Prior Publication Data

US 2008/0235836 P1 Sep. 25, 2008

(51) Int. Cl.
*A01H 5/00* (2006.01)

(52) U.S. Cl. ..... Plt./340

(58) Field of Classification Search ..... Plt./340
See application file for complete search history.

*Primary Examiner*—Kent L Bell
(74) *Attorney, Agent, or Firm*—The Webb Law Firm

(57) ABSTRACT

'Forever Midi Coral' is a new variety of *kalanchoe* that exhibits coral-colored flowers and small leaves with a long keeping quality.

1 Drawing Sheet

Botanical classification: *Kalanchoe blossfeldiana.*
Varietal denomination: 'Forever Midi Coral'.

BACKGROUND OF THE INVENTION

The present invention comprises a new and distinct cultivar of *Kalanchoe blossfeldiana* known by the varietal name 'Forever Midi Coral'. The new variety was discovered in Ashtabula, Ohio. The new variety is a result of cross breeding Seedling #95-362-10 (female parent) (unpatented) and Seedling #94-225-5 (male parent) (unpatented). The purpose of the breeding program was to develop a highly self-branching cultivar with a full, mounded flower cluster that was coral in color and had small leaves. Comparisons between the new variety and its parents cannot be made, as the parental varieties no longer exist. The new variety was first asexually reproduced by tip cuttings in Lompoc, Calif. The new variety has been trial and field tested and has been found to retain its distinctive characteristics and remain true to type through successive propagations. Characteristics that distinguish the new variety from others known to the breeder include:

- Mounded and compact growing habit;
- Coral flower color with a small white eye in the center;
- Early to flower, 9 to 9½ weeks from the start under short days;
- Able to be finished in 10 cm pots without growth regulators;
- Small leaf size;
- Does not heat delay in night temperatures above 22° C.;
- Long keeping quality with indeterminant growth habit; and
- Highly self-branched without pinching.

The new variety was grown in a 10 cm container in Lompoc, Calif. in a greenhouse under Dynaglass with 30% shade and 3500 to 4000 foot candles and 150 PPM nitrogen. The new variety was grown under natural, short days having temperatures of 20–22° C. and night temperatures of 16–18° C. The new variety initiates roots in 10 days at 21° C. The time to produce a rooted plant is 21 days at 21° C. Its rooting habit is dense and freely branching with fine and fibrous grey-white roots.

DESCRIPTION OF THE DRAWING

The accompanying photographic drawing illustrates the new variety, with the color being as nearly true as is possible with color illustrations of this type.

DESCRIPTION OF THE PLANT

Figure 1:
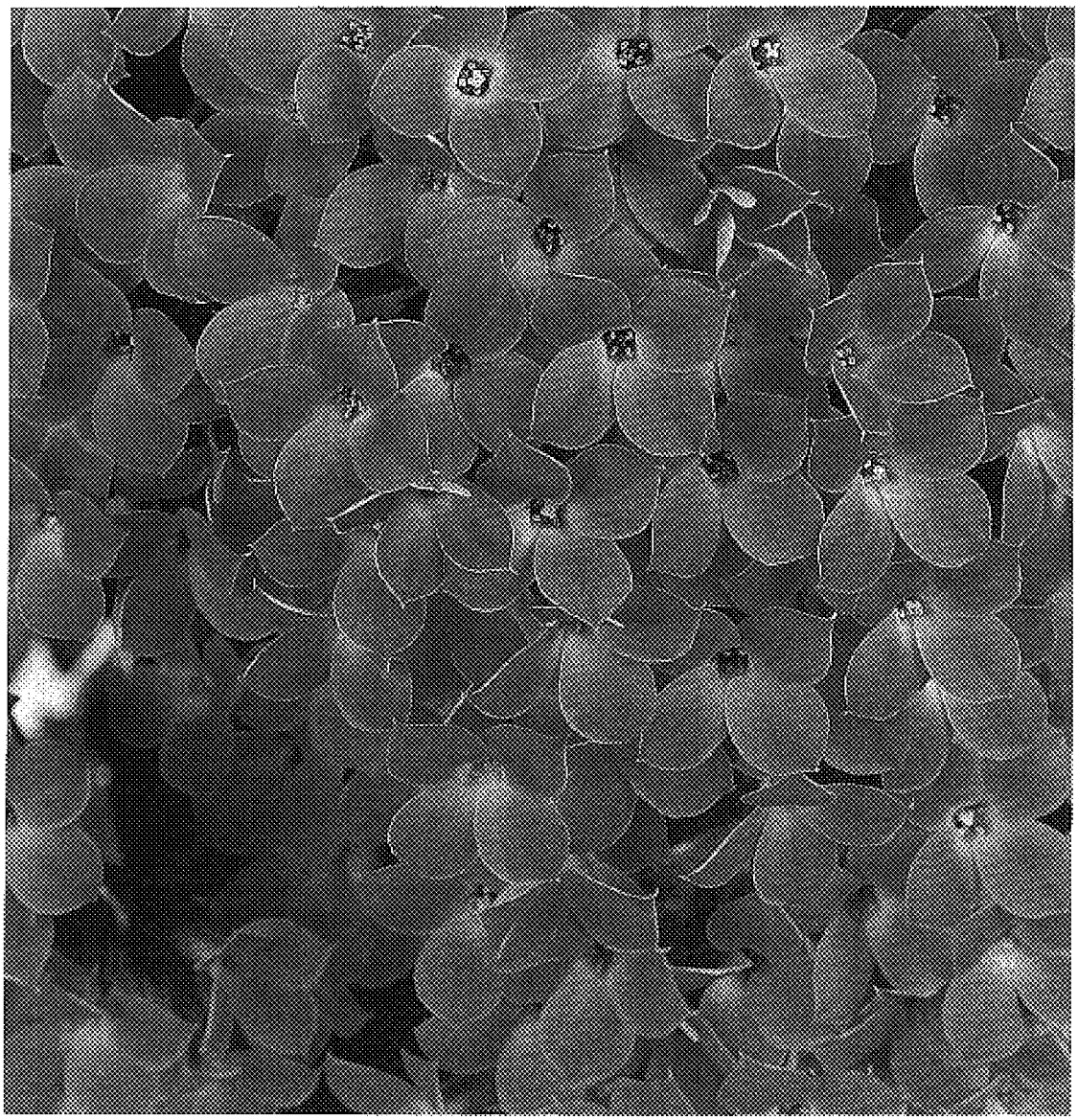

The following detailed description sets forth the characteristics of the new cultivar. The data which defines these characteristics were collected by asexual reproductions carried out in Lompoc, Calif. The color readings were taken indoors under 3500–4000 foot candles of light. The new variety was grown in a 10 cm container and was twelve weeks from the start of short days when described. Color references are primarily to the 1966 R.H.S. Colour Chart of The Royal Horticultural Society of London.

PLANT

Form: Mounded.
Height from soil to top of flowers: 15 cm.
Plant diameter: 22 to 25 cm.
Vigor: Vigorous.
Branching habit: Highly self-branching.
Main stem:
*Color.*—146B.
*Texture.*—Glabrous.
*Length.*—11 cm.
*Diameter.*—12 mm.
*Internode length.*—14 mm.
*Strength.*—Strong.
Lateral branches:
*Color.*—146B.
*Texture.*—Glabrous.

*Length.*—Basal: 12–13 cm. Upper: 8–10 cm.
*Diameter.*—13 mm.
*Internode length.*—3–8 mm.
*Strength.*—Strong.
*Quantity.*—8–10.

Foliage:
*Arrangement.*—Opposite.
*Number of leaves per stem.*—2.
*Size of leaf.*—Length: 8–9 cm. Width: 5.5–6.5 cm.
*Shape of leaf (generally).*—Ovate.
*Shape of apex.*—Acute.
*Shape of base.*—Acute.
*Texture.*—Glabrous, coriaceous and succulent.
*Aspect.*—45% angle to stem.
*Margin type.*—Crenate, moderately lobed.
*Fragrance.*—Shallow cut.
*Color.*—Young leaves: Upper surface: 146A. Lower surface: 146B. Mature leaves: Upper surface: 147A. Lower surface: 147B.
*Petiole.*—Length: 8–10 mm. Diameter: 6 mm. Color: 146B. Texture: Glabrous.
*Veins.*—Venation pattern: Pinnate. Color: Upper surface: 147A. Lower surface: 147B.

Flower

Natural flowering season: In January, in Lompoc, Calif. — Short days start around October 15$^{th}$.
Flower type and habit: Single, upright, cyme inflorescence.
Number of flowers per plant: 250 or more.
Time of day of flower opening: Morning, but takes 3 to 5 days to fully open.
Fragrance: None.
Longevity: Up to 2 weeks depending on environment.
Flower height: 13 mm including corolla tube.
Flower diameter: 15 mm.

Bud:
*Stage of development when described.*—Just before opening.
*Shape.*—Oblong.
*Diameter.*—3 mm.
*Length.*—15 mm.
*Color.*—39A near tip on mature bud; 144C calyx area.

Corolla:
*Diameter.*—4 mm.
*Depth.*—18 mm.
*Tube.*—Length: 12 mm. Diameter: 4 mm.

Petals:
*Arrangement.*—Whorl of 4 fused at base.
*Quantity.*—4.
*Length.*—8 mm; none fused part.
*Width.*—6 mm.
*Shape.*—Ovate to rounded.
*Apex.*—Cuspidate.
*Base.*—Acute.
*Margin.*—Entire.
*Texture.*—Smooth; soft.
*Color.*—Upper surface: 61D. Lower surface: 62C.

Sepals:
*Quantity.*—4.
*Shape.*—Lanceolate.
*Length.*—8 mm.
*Width.*—2 mm.
*Color.*—145B.

Peduncles:
*Length.*—20 mm.
*Diameter.*—3 mm.
*Color.*—146B.
*Texture.*—Glabrous.
*Orientation.*—45°angle.
*Strength.*—Strong.

Pedicels:
*Length.*—3 mm.
*Width.*—1 mm.
*Color.*—146B.

Disease resistance: Observed.
Weather tolerance: Not applicable — Mostly indoor flowering, pot crop.

Lasting quality:
*On plant.*—2 weeks or longer.
*Of cut flowers.*—Not applicable.

Seed production and description: None observed.
Fruit production and description: None observed.

REPRODUCTIVE ORGANS

Stamens:
*Number per flower.*—8.
*Filament length.*—8 mm approximately, 4 mm fuses to corolla.
*Anthers.*—Shape: Flat elliptical. Length: Less than 1 mm. Color: Yellow — Green.
*Pollen.*—Color: Yellow. Amount: Abundant.

Pistils:
*Length.*—10 mm.
*Styles.*—Length: 3 mm. Color: 144B.
*Stigma.*—Shape: Flat. Color: White when mature. Ovary color: 144A.

I claim:

1. A new and distinct variety of *kalanchoe* plant named 'Forever Midi Coral' as is herein described and illustrated.

* * * * *

UNITED STATES PATENT AND TRADEMARK OFFICE

CERTIFICATE OF CORRECTION

PATENT NO. : PP 19,987 P3
APPLICATION NO. : 11/728029
DATED : May 12, 2009
INVENTOR(S) : Drewlow It is certified that error appears in the above-identified patent and that said Letters Patent is hereby corrected as shown below:

Column 3, line 2, "*Diameter*.—13 mm." should read -- *Diameter*.— 3 mm. --

Signed and Sealed this

Fifteenth Day of September, 2009

David J. Kappos

David J. Kappos
*Director of the United States Patent and Trademark Office*